(12) United States Patent
West

(10) Patent No.: US 6,506,915 B1
(45) Date of Patent: Jan. 14, 2003

(54) SYNTHESIS OF COENZYME Q10 UBIQUINONE

(76) Inventor: Daniel David West, 1 Warren Ct., Rockport, ME (US) 01966

( * ) Notice: Subject to any disclaimer, the term of this patent is extended or adjusted under 35 U.S.C. 154(b) by 0 days.

(21) Appl. No.: 09/880,642

(22) Filed: Jun. 14, 2001

(51) Int. Cl.$^7$ ................................................ C07C 50/06
(52) U.S. Cl. ...................................................... 552/293
(58) Field of Search ........................................... 552/293

*Primary Examiner*—Barbara P. Badio
(74) *Attorney, Agent, or Firm*—Evelyn M. Sommer

(57) ABSTRACT

Processes for the stereospecific synthesis of coenzyme Q10, ubiquinone, are disclosed; a total synthetic procedure using geraniol as the starting material. The process of the invention results in high yields of isometrically pure ubiquinone. The synthetic coenzyme Q10 can be used as an antioxidant, a nutritional supplement and as a pharmaceutical in treating many conditions.

1 Claim, No Drawings

SYNTHESIS OF COENZYME Q10 UBIQUINONE

BACKGROUND OF THE INVENTION

The invention relates to an improved process for the stereospecific synthesis of Coenzyme Q10, ubiquinone. The present invention also relates to the therapeutically useful optically pure isomers of Coenzyme 10 and refers to new pharmaceutical compositions which contain the optically pure isomers of coenzyme Q10 dissolved or suspended in a suitable vehicle which are useful for example in preventing anoxic tissular damage, particularly in the myocardium. Previous procedures for ubiquinone isolation had several drawbacks; many steps were involved, the yields were low, the intermediates were difficult to purify, overall costs were high, and the final products were obtained as mixtures of isomers, cis(Z) and trans (E).

Coenzyme Q gives reference to a series of quinones which are widely distributed in animals, plants and microorganisms. These quinones have been shown to function in biological electron transport systems which are responsible for energy conversion within living cells. In structure, the coenzyme Q group closely resembles the members of the vitamin K group and the tocopherylquinones, which are derived from tocopherols (vitamin E), in that they all possess a quinone ring attached to a long hydrocarbon tail. The quinones of the coenzyme Q series which are found in various biological species differ only slightly in chemical structure and form a group of related, 2-3-dimethoxy-5-methyl-benzoquinones with a polyisoprenoid side chain in the 6-position which varies in length from 30 to 50 carbon atoms. Since each isoprenoid unit in the chain contains five carbon atoms, the number of isoprenoid units in the side chain varies from 6 to 10. The different numbers of the groups have been designated by a subscript following the Q to denote the number of isoprenoid units in the side chain, as in Q10. Difference in properties are due to the difference in length of the side chain. The members of the group known to occur naturally are Q6 through Q10. Coenzyme Q functions as an agent for carrying out oxidation and reduction within cells. Its primary site of function is in the terminal electron transport system where it acts as an electron or hydrogen carrier between the flavoproteins (which catalyze the oxidation of succinate and reduced pyridine nucleotides) and the cytochromes. This process, is carried out in the mitochondria of cells of higher organisms. Certain bacteria and lower organisms do not contain any coenzyme Q. It has been shown that many of these organisms contain vitamin K, instead and that this quinone functions in electron transport in much the same way as coenzyme Q. Similarly, plant chloroplasts do not contain coenzyme Q, but do contain plastoquinones, which are structurally related to coenzyme Q. Plastoquinone functions in the electron transport process involved in photosynthesis. In some organisms, coenzyme Q is present together with other quinones, such as vitamin K, tocopherylquinones, and plastoquinones; and each type of quinone can carry out different parts of the electron transport functions.

Coenzyme Q10, is a ubiquinone. Ubiquinones are a class of lipid soluble benzoquinones that are involved in mitochondrial electron transport and are essential electron and proton carriers that function in the production of biochemical energy in all cells of aerobic organisms; participating in the transport of electrons from organic substrates to oxygen in the respiratory chain of mitochondria. In addition, coenzyme Q10 has antioxidant and membrane stabilizing properties that serve to prevent cellular damage resulting from normal metabolic processes. It plays an important role as an antioxidant to neutralize potentially damaging free radicals created in part by the energy-generating process. As an energy carrier, coenzyme Q10 is continually going through an oxidation reduction cycle. As each coenzyme Q10 molecule accepts electrons, it is reduced, when it gives up electrons, it becomes oxidized again. In coenzyme Q10's reduced form (ubiquinol), the coenzyme Q10 molecule holds electrons loosely and will quite easily give up one or two electrons to neutralize free radicals. In its electron rich reduced form, coenzyme Q10 is as potent an antioxidant as vitamin E. Coenzyme Q10's main role as an antioxidant is in the mitochondria where it first participates in the process by which free radicals are generated and then helps to quench the extra free radicals that threaten cellular components such as DNA, RNA, and cell membranes. One of coenzyme Q10's key antioxidant actions is within the cell membrane, where it counters the oxidative attack of polyunsaturated lipids (lipid peroxidation), which causes damage in a self-propagating, destructive chain reaction that ultimately results in membrane degeneration leading to cell death.

In mammalian tissue the quinone ring of coenzyme Q10 is synthesized from the amino acids, tyrosine and phenylalanine and the polyprenyl side chain is synthesized from acetyl-CoA. The number of isoprene units depends on the species, the most common form in mammals contains ten isoprene units. Coenzyme Q10 participates in the transport of electrons from organic substrates to oxygen in the respiratory chain of the mitochondria. During this process ubiquinone is reduced to a free radical semiquinone by the uptake of a single electron. Reduction of this enzyme-bound intermediate by a second electron yields ubiquinol. This a reversible reducible process.

Ubiquinone has a characteristic light absorption band at 270 to 290 nm, which disappears when it is reduced to its quinol form; this spectral change is used to measure oxidation and reduction of ubiquinone.

The structure of coenzyme Q10 consists of a quinone ring attached to an isoprene side chain. It contains 82.08% carbon, 10.51% hydrogen and 7.41% oxygen. Its has a molecular weight of 863.37 and a formula of $C_{59}H_{90}O_4$. The oxidized, intermediate and reduced forms of coenzyme Q10 are shown in the following drawings:

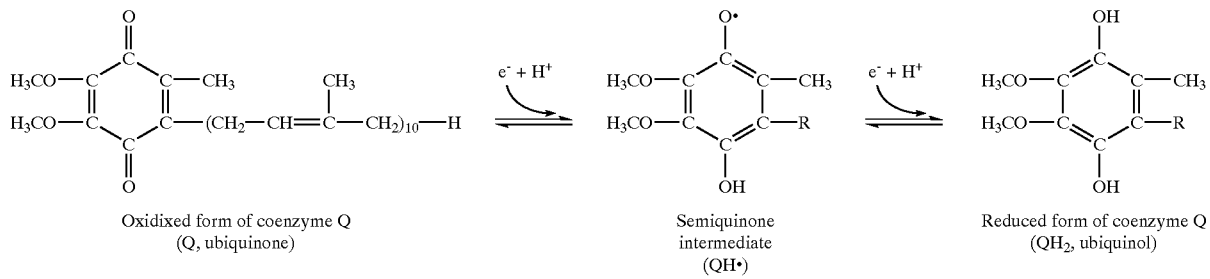

Oxidixed form of coenzyme Q (Q, ubiquinone)

Semiquinone intermediate (QH•)

Reduced form of coenzyme Q (QH₂, ubiquinol)

Ubiquinone (Q) is reduced to ubiquinol (QH$_2$) through a semiquinone intermediate (QH$^-$).

Coenzyme Q10 is used extensively as a nutritional supplement as well as a pharmacological active agent. It has wide use and acceptance in the treatment of cardiovascular disease in traditional as well as alternative medicine. It is used successfully in treating ischemic heart disease, chronic heart failure, toxin induced cardiomyopathy, hypertension and hyperlipidemia. Endogenous coenzyme Q10 functions as an essential cofactor in many metabolic pathways. Its action as an additional pharmacological agent in treatment of such cardiovascular disease processes may be to improve function of the involved tissues that are ischemic or pathologically altered by providing an increased energy source, by acting as a free radical scavenger and/or membrane stabilizer. In addition, coenzyme Q10 is found in high concentrations in healthy hearts and at low levels in people with congestive failure leading to the suggestion that supplementation with the coenzyme would be of help in the treatment of heart disease. It is theorized that Coenzyme Q10 might work in the heart in two ways; as an antioxidant to help thwart damage from free radicals that contribute to arterial blockage, and to help boost heart muscle action by improving energy efficiency. Additionally coenzyme Q10 may boost the effects of vitamin E, also a potent antioxidant with some potential beneficial heart effects.

Coenzyme Q10 has been used in the treatment of slow muscle degeneration (dystrophy or atrophy) and the accompanying cardiac complications typically found in these patients.

In addition to its helper role in the release of energy, Coenzyme Q10 serves as an antioxidant, neutralizing free radicals that cause potentially irreversible damage to cells, tissues, and organs. Coenzyme Q10 is also believed to strengthen the immune system, so as to provide antibacterial and antiviral activity (including HIV), to increase antibody production and to induce the immune system to produce a greater number of immune acting cells. Among the increasing number of pharmacological uses ascribed to coenzyme Q10 are anticancer (in particular breast cancer) activity, in the treatment of periodontal disease, diabetes, Parkinson's, Alzheimer's, Huntington's disease and to help counteract the aging process.

The rationale for its effectiveness in relieving certain brain disorders is that coenzyme Q10 temporarily restores mitochondrial activity in cells. There is evidence that Parkinson's disease, Huntington's disease and some other neurological diseases may impair the mitochondria throughout the body, but particularly in nerve and brain cells. In that case coenzyme Q10 might slow the progression of these diseases. As a potent. antioxidant, coenzyme Q10 might also help prevent the cell death that occurs in these diseases by blocking the buildup of toxic substances. It has also been shown, that coenzyme Q10 lowers levels of lactate in the brains of people with Huntington's disease. Increased lactate suggests a problem with energy metabolism in brain cells.

Free radical damage is thought to be an important contributor to the body wide deterioration that accompanies aging. Laboratory evidence suggests that supplementation with Coenzyme Q10 can at least partially protect against such damage.

It is clear from the literature that activity of coenzyme Q10 is strictly connected with the tissular respiratory processes.

A wide bibliography points out its ability to solve or prevent anoxic tissular damages, particularly in the myocardium.

Other positive effects have been obtained by means of coenzyme Q10 in the treatment of arterial hypertension, of muscular dystrophy, of periodontopathies, of penfigus and of lichen planus.

In all such pathological conditions, it was also noticed that the administration of coenzyme Q10 led to a normalization of tissular concentrations of this enzyme, otherwise scarce.

Coenzyme Q10 is not toxic (there are no reported side effects), no known medical conditions preclude it use. It is generally employed as a supplement, rather than a replacement for standard medical treatment. No known drug interactions have been reported. Daily oral doses vary from 5–10 mg/dosage (15 to 30 mg pro die) to 50–100 mg/dosage (100–200 mg pro die) The administration of even higher dosages up to 400 mg pro die give satisfactory clinical results but it increases sometimes, the pro die effects of the drug. The larger amount usually being given as multiple doses.

There seems to be no limiting factor as to how long the coenzyme Q10 may be taken; individuals have used it continuously for years.

DESCRIPTION OF THE INVENTION

This invention relates to a process for the stereospecific synthesis of coenzyme Q10, ubiquinone. In accordance with the invention described in co-pending application Ser. No. 09/837,320 filed Apr. 19, 2001, there is disclosed a semi synthetic procedure for the synthesis of coenzyme Q10 using solanesol as the starting material.

When solanesol derived from tobacco and potato leaves is used as the starting material, the method of production of coenzyme Q10 involves a semi synthesis. If geraniol is used as the starting material what is involved is a total synthesis. The method of synthesis as hereinafter set forth produces high yields of isomerically pure coenzyme Q10.

The previous methods of production of Coenzyme Q10 had many disadvantages. The procedures were lengthy and involved many steps, the resulting yields were low, the intermediates were difficult to purify, overall costs were high and the final products were obtained as mixtures of isomers, cis(Z) and trans(E).

In addition to alleviating the described disadvantages, the processes of the present invention have been found to be stereospecific (selective) producing exclusively the desired all trans(E) isomers.

The following example will serve to illustrate the invention, it being understood that the same is not to be construed in limitation thereof.

EXAMPLE

Step 1:—2,3,4,5(tetramethoxy)-6-geranyltoluene

120 MI n-butyl-lithium in 1.1 M hexane) was added over ½ hour under N$_2$ to a solution of 20 g 2,3,4,5-tetromethoxy toluene (prepared in step 5 of the Example in co-pending application Ser. No. 09/837,320, which is incorporated herein by reference thereto) in 200 ml hexane containing N,N,N,N-tetramethylethylenediamine (20 g) at 0 degrees C. The mixture is stirred for an additional ½ hour. While continuing the stirring, a solution of geranyl bromide (20 g) in 200 ml THF is added slowly over a one hour period and then the stirring is continued for an additional hour. The mixture is then quenched with saturated aqueous sodium chloride, 1 liter of ether is then added and the organic phase separated and washed with aqueous sodium hydroxide, water and brine and dried over magnesium sulfate. The solvent is then evaporated and the residue chromatographed on silica gel (hexane/ethylacetate 25:1) to give 22 g of colorless oil.

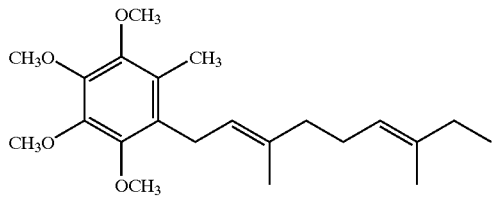

Step 2—6,7 Epoxygeranyl 1,2,3,4,5,-tetramethoxytoluene

To a solution of 38 g of 2,3,4,5,-tetramethoxy-6-geranyltoluene produced in step 1, in 300 ml methyl chloride, there is added over a period of ½ hour, a solution of m-chloroperoxybenzoic acid (MCPBA)(30 g, 85%) in 300 ml methyl chloride at 0 degree C. The reaction mixture is stirred at 0 C. for 1 hr, quenched with saturated aqueous sodium bicarbonate and water and dried over magnesium sulfate. The solvent is evaporated and the products dried and chromatographed on silica gel (hexane/ether, 5:1) to give 20 g of colorless oil.

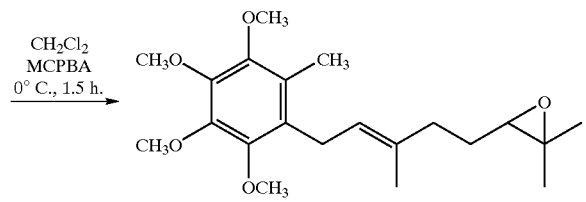

Step 3:—Di-isopropyl(4-E)-1-isopropenyl-4-methyl-6-(2,3,4,5-tetramethoxytoluene)-4-hexenyl)phosphate To a solution of (1-pr) 2 Na1E+2 in ether/hexane (825 ml) there is added a solution of the product obtained in step 2 (20 g) in 170 ml hexane at 0 degree C. drop wise over ½ hour. The mixture is stirred an additional ½ hour, and quenched with 1 l of I N HCl. 500 ml of ether are added and the organic phase separated, washed with 1 l brine and dried with magnesium sulfate. The solvent is evaporated and placed in 200 ml THF, butyl lithium (Buli) in 37.5 ML hexane (1.6 M) is added drop wise at 78 degree C. under stirring for ½ hour and then the stirring continued at 0 degree C. for 10 minutes. Di-isopropyl chlorophosphate (20 g) is then added still maintaining the 0 degree C. temperature while stirring for 15 minutes. The mixture is quenched with saturated ammonium chloride (9.2 l) and then the organic layer is separated. The aqueous layer is extracted with 200 ml of ether. The combined layers are dried with magnesium sulfate and concentrated. The product is chromatographed on silica gel (hexane/ether. 1:4) to give 28.5 g of colorless oil

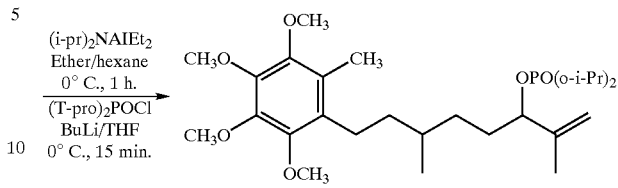

Step 4:—1-(2E,6E,10E,14E,18E), 3,7,11,15,19,23-hexamethyl-2,6,10,14,18,22-tetracosahexadenyl-2,3,4,5 tetramethoxytoluene To a solution of geranylgeranylmagnesium chloride prepared from magnesium turnings (36.5 g) and geranylgeranyl chloride (93 g) in 300 ml THF there is added a solution of CuCN (33 g) and LiCl (30 g) in 300 ml THF at −30 degree C. The mixture is stirred at that temperature for 10 minutes and then at 0 degree C. for 20 minutes. The resulting black solution is cooled to −78 degrees C. and a solution of 16 g di-isopropyl (4-E)-1 isopropenyl-4-methyl-6-(2,3,4,5-tetromethoxy toluene prepared in step 3 in 20 ml THF is added drop wise at −78 degree C. The solution is then stirred at −60 degree C. for 2 hours, and then quenched with 9.8 l of 2 N HCl. The organic layer is separated and the aqueous layer extracted with 500 ml of ether. The combined organic layers are washed with 800 ml of 2N NaOH and 800 ml of brine and dried with magnesium sulfate. The solvent is evaporated and the product chromatographed on silica gel (hexane/ether, (15:1)

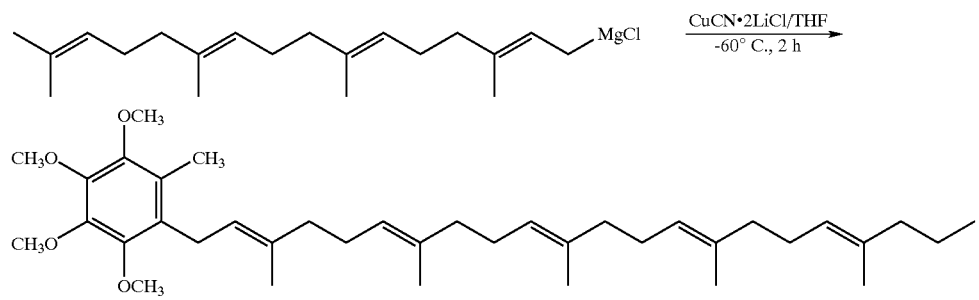

Step 5:—1-(2E,6E,10E,14E,18E)-22,23-epoxy 3,7,1,1,15,19,23-hexamethyl-2,6,10,14.18-tetracosapentaenyl-2,3,4,5,-tetramethoxytoluene To a solution, prepared from the product obtained from step 4, containing 22 g in 1 ml water and 80 ml THF, 10 g N-bromosuccinimide (NBS) are added in portion wise fashion. After stirring at room temperature for 1 hour, 80 ml of water are added. The aqueous layer is extracted 2 times with ether (80 ml for each extraction and the combined organic layer dried over magnesium sulfate. Filtration and concentration provide the crude bromohydrin as an oil, which is then dissolved in 80 ml methyl alcohol. A solution is added then a solution of sodium methyl aldehyde in methanol (28%, 11 g) is added to the resultant solution, drop wise at 0 degree C. After stirring at 0 degree C. for ½ hour, 200 ml of ether mixed with 100 ml of water are added. The organic layer is

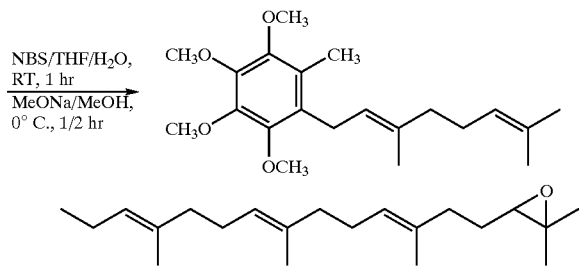

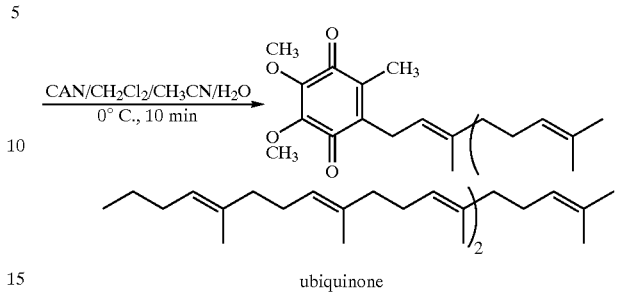

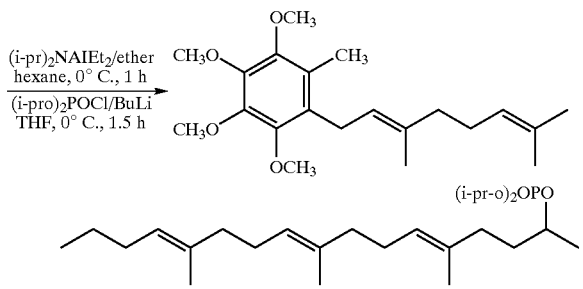

Step 6:—Di-isopropyl (4E,8E,12E,16E,20E)-1-isopropenyl-4,8,12,16,20-pentamethyl-22-(2,3,4,5-tetramethoxy)-4,8,12,20-docosapentaenyl)phosphate This was prepared from the 1(2E,6E,10E,14E,18E)-22,23-epoxy-3,7,1,1,15,19,23-hexamethyl-2,6,10,14,18-tetracosapentaenyl-2,3,4,5-tetra methoxytoluene according to the procedure set out in accordance with the method of step 5 and the conditions of step 3. An 85% yield was obtained after chromatography (hexane/ether 1:2).

Step 7:—1(2E,6E,10E,14E,18E,22E,26E,30E.34E)-3,7,11,15,19,23,27,31,35,39-decamethyl-2,6,1,14,18,22,26,30,34,38-tetracontadecaenyl-2,3,4,5-tetramethoxytoluene This product was prepared using the product obtained in step 6 using the conditions described in step 4. A 98% yield was obtained after chromatography (hexane/ether 10:1).

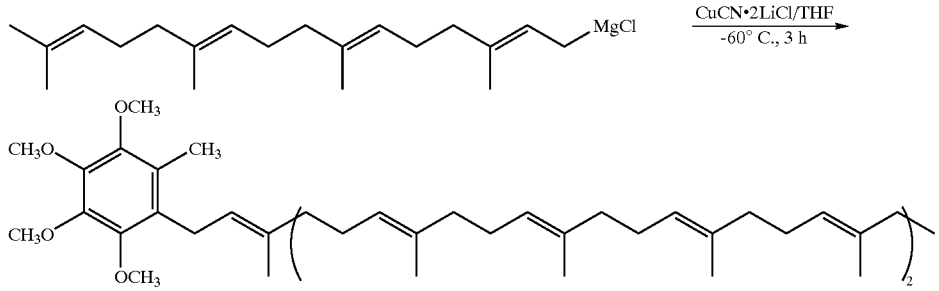

Step 8: Ubiquinone

To a solution 15.5 g uf of the product produced in step 7 in a mixture of 70 ml methyl cyanide and 70 ml of methyl chloride there is added a solution of ceric ammonium nitrate (CAN) (920 g) in 50% aqueous methyl cyanide (140 ml), drop wise over a period of 5 minutes at 0 degree C. After stirring for 5 minutes, 1 liter of water is added and the crude product extracted with 1 liter of ether, washed with 5% aqueous sodium bicarbonate and 1 liter of water, dried over magnesium sulfate and concentrated. The oil is chromatographed on silica gel (hexane/ether 10:1) to give 12 g ubiquinone as yellow solid.

The administration of optically pure Coenzyme Q10 can be oral, parenteral or topically, in the latter case for the treatment of diseases of skin and mucous membranes. Oral administration is favored over parenteral administration due to the very low solubility of coenzyme Q10 in excipients compatible with is parenteral administration. Oral administration has proved particularly useful in the treatment of diseases affecting metabolically very active organs, whereas coenzyme Q10 if administered orally proves to be substantially ineffective at the cutaneous level. Accordingly the concentration of Coenzyme Q10 has to be increased for topical administration directly to impaired or damaged tissue.

The oral form of administration can be as pills, tablets, capsules or liquid preparations in each case formulated in the conventional manner with suitable carriers and formulation aids. The formulations are prepared to deliver 5–100 mg per dosage unit and in some instances up to 200 mg per dosage units of the optically pure coenzyme Q10.

The compositions for topical administration can be prepared by dissolving or suspending coenzyme Q10 in vegetable oils such as corn oil, canola oil, or soy bean oil, lecithin, glycerol, glycerylfurole, Tween 80 or other derivatives, suspending agents or diluents. After the addition of suitable carriers and formulation aids to such solutions or suspensions, the compositions can be formulated as pastes, creams, ointments, gels, lotions, unguents.

The compositions for topical application contain the optically pure coenzyme 10 as the active principal in amounts from 0.1 to 10%, preferably from 0.25 to 1%. The topical compositions can also be used for cosmethological purposes. In such a case, the content of coenzyme Q10 can be lower than the limits aforementioned being preferably from 0.0001 to 0.1%.

The compositions in any application form may also contain other topically active components beside the active principle (optically active coenzyme Q10)

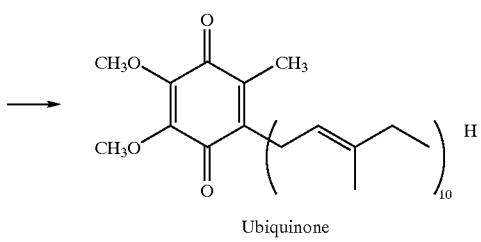

Ubiquinone

What is claimed is:

1. A process for the stereo specific synthesis of optically pure trans (E)isomer of coenzyme Q10 which comprises the following steps:

1. preparing 2,3,4,5-tetramethoxy-6-geranyltoluene having the formula

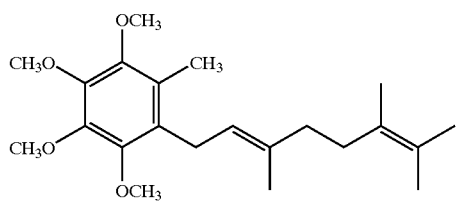

by reacting geranyl bromine with 2,3,4,5-tetramethoxy toluene having the formula

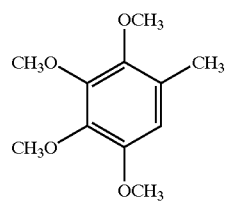

2. reacting the 2,3,4,5-tetramethoxy-6-geranyl toluene thus obtained as follows, to provide 6,7-epoxy geranyl 1,2,3,4,5-tetramethoxytoluene

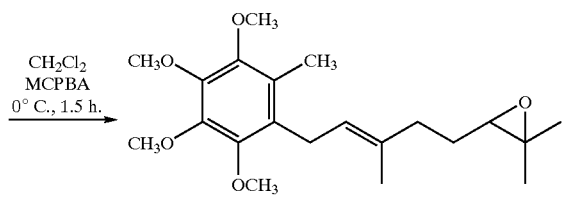

3. reacting the 6,7-epoxy geranyl 1,2,3,4,5-tetramethoxy toluene as follows to form di-isopropyl (4E)-1-isopropenyl-4-methyl-6 (2,3,4,5-tetramethoxytoluene-4-hexenyl)phosphate

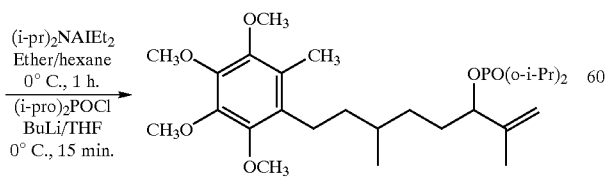

4. reacting the di-isopropyl (4E)-1-isopropenyl4-methyl-6-(2,3,4,5-tetamethoxytoluene 4-hexenyl phosphate with geranyl geranyl magnesium chloride as follows to form 1-(2E,6E,10E,14E,18E)3,7,11,15,19,23-hexamethyl-2,6,10,14,18,22-tetracosahexadenyl-2,3,4,5-tetramethoxytoluene

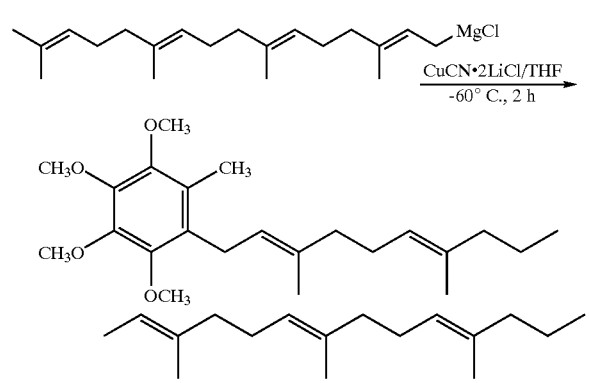

5. reacting the 1-(2E,6E,10E,14E,18E),3,7,11,15,19,23-hexamethyl-2,6,10,14,18,22-tetracosahexadenyl-2,3,4,5-tetramethoxy toluene formed as follows to form 1-(2E, 6E,10E,14E,18E)-22,23-epoxy-3,7,11,15,19,23-hexamethyl-2,6,10,14,18, tetracosapentenyl-2,3,4,5-tetramethoxy toluene

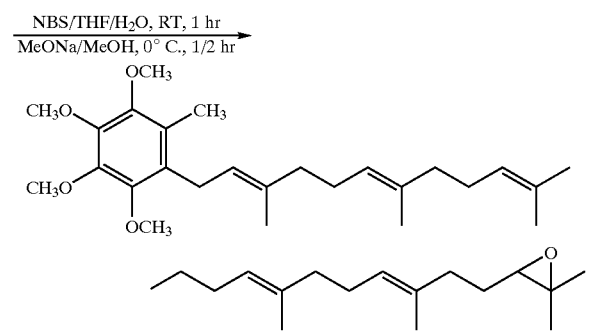

6. reacting the 1-(2E,6E,10E,14E,18E)-22,23-epoxy-3,7, 11,15,19,23-hexamethyl-2,6,10,14,18-tetracosapentaenyl-2,3,4,5-tetramethoxytoluene formed as follows to yield di-isopropyl (4E,8E,12E, 16E,20E)-1-isopropenyl-4,8,12,16,20-pentamethyl-22-(2,3,4,5-tetramethoxy-4,8,12,20-docosapentaenyl-phosphate

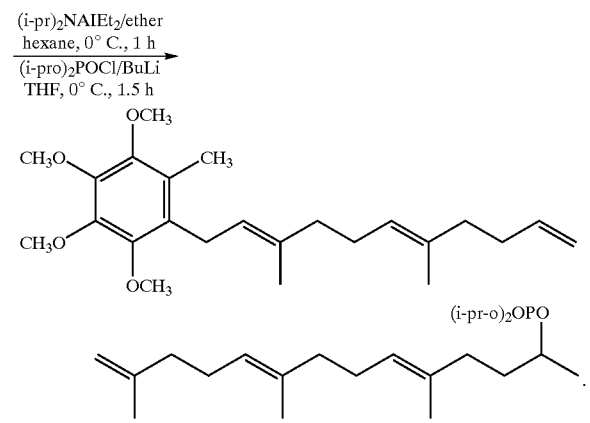

7. reacting the di-isopropyl (4E,8E,12E,16E,20E)-1-isopropenyl-4,8,12,16,20-pentamethyl-22-(2,3,4,5- tetramethoxy-4,8,12,20-docosapentaenyl-phosphate) formed as follows forming 1-(2E,6E,10E,14E,18E, 22E,26E,30E,34E)-3,7,11,15,19,23,27,31,35,39-decamethyl-2,6,10,14,18,22,26,30,34,38-tetracontadecaenyl-2,3,4,5-tetramethoxytoluene
8. and reacting the product of the immediately preceding step 7 as follows to form the optically pure trans(E) isomer of coenzyme Q10
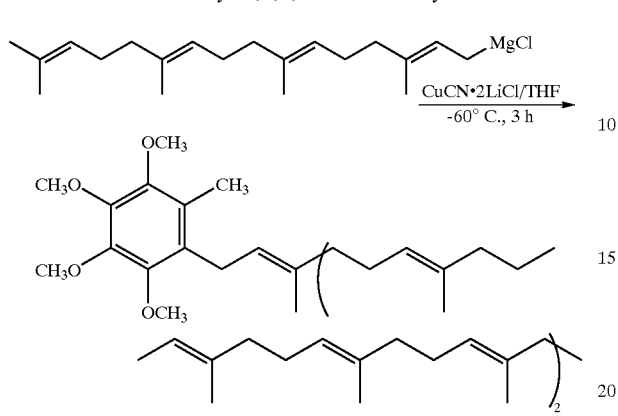
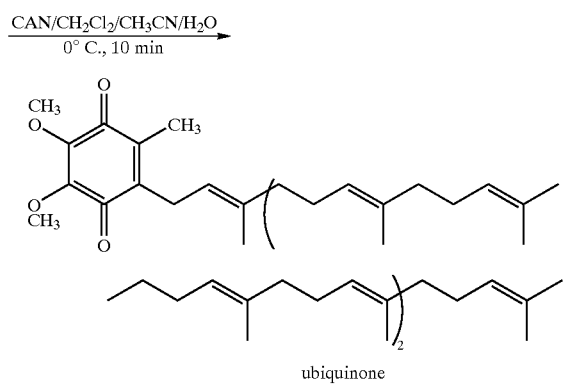
ubiquinone
* * * * *